(12) United States Patent
Hirokawa et al.

(10) Patent No.: US 8,507,223 B2
(45) Date of Patent: Aug. 13, 2013

(54) METHOD FOR QUANTITATIVE DETERMINATION OF GLYCATED PROTEIN AND KIT FOR QUANTITATIVE DETERMINATION OF THE SAME

(75) Inventors: Kozo Hirokawa, Chiba (JP); Kazuhiko Shimoji, Chiba (JP)

(73) Assignee: Kikkoman Corporation, Chiba (JP)

( * ) Notice: Subject to any disclaimer, the term of this patent is extended or adjusted under 35 U.S.C. 154(b) by 1069 days.

(21) Appl. No.: 11/994,796

(22) PCT Filed: Jul. 19, 2006

(86) PCT No.: PCT/JP2006/314299
§ 371 (c)(1),
(2), (4) Date: Jan. 4, 2008

(87) PCT Pub. No.: WO2007/010950
PCT Pub. Date: Jan. 25, 2007

(65) Prior Publication Data
US 2008/0193960 A1    Aug. 14, 2008

(30) Foreign Application Priority Data
Jul. 19, 2005    (JP) ................................ 2005-208737

(51) Int. Cl.
*C12P 21/04*    (2006.01)

(52) U.S. Cl.
USPC ...................................................... 435/69.6

(58) Field of Classification Search
None
See application file for complete search history.

(56) References Cited

U.S. PATENT DOCUMENTS

| | | | |
|---|---|---|---|
| 7,449,305 B2 | 11/2008 | Yonehara et al. | |
| 2005/0101771 A1 | 5/2005 | Kouzuma et al. | |
| 2007/0178547 A1 | 8/2007 | Taniguchi et al. | |
| 2008/0113381 A1 | 5/2008 | Matsuoka et al. | |

FOREIGN PATENT DOCUMENTS

| | | |
|---|---|---|
| EP | 1 223 224 A1 | 7/2002 |
| EP | 1 304 385 A1 | 4/2003 |
| EP | 1 477 569 A1 | 11/2004 |
| EP | 1 693 461 A1 | 8/2006 |
| JP | 2000-300294 | 10/2000 |
| JP | 2001 057897 A2 | 3/2001 |
| JP | 2003 079386 A2 | 3/2003 |
| JP | 2003 274976 A2 | 9/2003 |
| JP | 2004-113014 | 4/2004 |
| JP | 2005-110657 | 4/2005 |
| WO | WO 96/34977 | 11/1996 |
| WO | WO-02/061119 A | 8/2002 |
| WO | WO 03/033729 A1 | 4/2003 |
| WO | WO 2004/104203 | 12/2004 |
| WO | WO 2005/087946 A1 | 9/2005 |

OTHER PUBLICATIONS

Sakurabayashi et al. "New enzmatic assay for glycohemoglobin", Clinical Chemistry, 2003, 49(2):269-274.*
Hirokawa et al. "Enzymes used for the determination of HbA1c", FEMS Microbiology Letters, 2004, 235:157-162.*
Hirokawa et al. "An enzymatic method for the determination of hemoglobinA1c", Biotechnology Letters, 2005, 27:963-968.*
Kozo Hirokawa et al., "An enzymatic method for the determination of hemoglobin$A_{1c}$", Biotechnology Letters (2005) 27: 963-968.
European Search Report Appln. No. 06781266.9—Nov. 24, 2008.
Ghislain Delpierre et al., "Identification of Fructosamine Residues Deglycated by Fructosamine-3-kinase in Human Hemoglobin", The Journal of Biological Chemistry, vol. 279, No. 26, Issue of Jun. 25, 2004, pp. 27613-27620.
Official Notification JP Patent Application No. 2007-526037.
Office Action in JP Appln No. 2007-526037 dated Jul. 3, 2012.

* cited by examiner

*Primary Examiner* — Bin Shen
(74) *Attorney, Agent, or Firm* — Foley & Lardner LLP

(57) ABSTRACT

The present invention relates to a method for quantitative determination of an α-glycated peptide in a sample, comprising causing protease to act on a whole blood and/or blood cell sample, causing an elimination reagent containing one or a plurality of types of ketoamine oxidase to act on the resultant, eliminating an α-glycated amino acid, an ε-glycated amino acid, an ε-glycated peptide, or a combination thereof, and then determining the α-glycated peptide in the sample using oxidase that acts on the α-glycated peptide. The present invention also relates to an elimination reagent and a kit to be used for such method. According to the present invention, measurement errors in quantitative determination of a glycated protein such as glycated hemoglobin can be reduced, and thus a precise measured value can be obtained.

6 Claims, No Drawings

SEQUENCE LISTING

<160> NUMBER OF SEQ ID NOS: 1

<210> SEQ ID NO 1
<211> LENGTH: 6
<212> TYPE: PRT
<213> ORGANISM: Homo sapiens

<400> SEQUENCE: 1

Val His Leu Thr Pro Glu
 1               5

METHOD FOR QUANTITATIVE DETERMINATION OF GLYCATED PROTEIN AND KIT FOR QUANTITATIVE DETERMINATION OF THE SAME

TECHNICAL FIELD

The present invention relates to a method for quantitative determination of a glycated protein, which is intended for use in obtaining a precise measured value via reduction in measurement error upon quantitative determination of a glycated protein such as glycated hemoglobin, a reagent for eliminating substances that cause measurement errors, and a kit for determination of a glycated protein.

BACKGROUND ART

Glycated protein is nonenzymatically-glycated protein. Specifically, the glycated protein is generated as a result of nonenzymatical covalent bonding between an aldehyde group on the sugar; that is, on the aldose side (a monosaccharide potentially having an aldehyde group and its derivative) and an amino group on the protein side. Examples of such amino group on the protein side include N-terminal α-amino group and side-chain ε-amino group of internal lysine residue. α-glycated protein and/or ε-glycated protein is generated by glycation of these groups. Furthermore, such glycated protein is formed when a Schiff base generated as a reaction intermediate is subjected to Amadori rearrangement. Thus, the glycated protein is also referred to as a so-called Amadori compound.

The glycated protein is contained in body fluids such as in vivo blood or biological samples such as hair. Examples of such glycated protein existing in blood include glycated hemoglobin and glycoalbumin. Generation of such glycated protein strongly depends on the concentrations of saccharides such as glucose, which are dissolved in sera. Under diabetic conditions, it is known that glycated protein generation is enhanced. Furthermore, glycoalbumin or glycated hemoglobin is used as an indicator that reflects a blood glucose level for diagnosing or controlling the symptoms of diabetes. In particular, glycated hemoglobin contained in erythrocytes reflects a past average blood glucose level for a certain time period. Hence, quantitative determination of such glycated protein as an indicator is important for diagnosing or controlling the symptoms of diabetes.

A method that is conventionally known as an enzymatic method for quantitative determination of glycated protein and is intended for use in diagnosing diabetes involves digesting a glycated protein to be determined with protease or the like, liberating glycated peptide or glycated amino acid, and quantitatively determining the subject glycated protein using enzymes that specifically act thereon. Another example of a known method involves determining a glycated amino acid derived from glycated hemoglobin or glycoalbumin using oxidase that acts on the glycated amino acid (see JP Patent Publication (Kokoku) No. 5-33997 B (1993); JP Patent Publication (Kokoku) No. 6-65300 B (1994); JP Patent Publication (Kokai) No. 5-192193 A (1993); JP Patent Publication (Kokai) No. 6-46846 (1994) A; and International Publication No. 97/13872 Pamphlet). Furthermore, a method disclosed by the applicant relates to quantitative determination of hemoglobin A1c (glycated protein in which glucose binds to an α-amino group of hemoglobin "β chain" N-terminal Val (valine), hereinafter referred to as HbA1c), the precise quantitative determination of which has been difficult with the above methods, and uses an enzyme (fructosyl peptide oxidase) that acts on an α-glycated peptide (see JP Patent Publication (Kokai) No. 2001-95598 A).

There are 4 types of glycated amino acid or glycated peptide that can be liberated from a glycated protein in connection with the above various types of determination and can serve as subjects for determination: α-glycated amino acid, α-glycated peptide, ε-glycated amino acid, and ε-glycated peptide. α-glycated amino acids and α-glycated peptides are generated via their liberation from the glycated N-termini of glycated proteins. Meanwhile, an ε-glycated amino acid and an ε-glycated peptide are generated via their liberation from positions where the ε-side chains of amino acids are glycated (for example, glycation can take place at a lysine residue or an arginine residue within the protein).

For example, for quantitative determination of glycoalbumin, the sum of the amount of ε-glycated amino acid and the amount of ε-glycated peptide is measured. For quantitative determination of HbA1c, α-glycated peptide determination is performed, for example. Depending on glycated protein types to be determined, different glycated amino acids and/or glycated peptides are each determined using an enzyme having high specificity thereto. At this time, if the amount or the concentration of a target glycated amino acid or glycated peptide (that is cleaved by protease from a true determination subject) includes an amount or concentration of glycated amino acids or glycated peptides other than the target, a measured value higher than the actual measured value of the target (specific) glycated amino acid or glycated peptide is obtained. Thus, a measurement error is generated. As a countermeasure for such problem, 2 methods relating to quantitative determination of glycated hemoglobin have been disclosed, which involve eliminating glycated amino acids or glycated peptides other than a substance to be determined (see International Publication No. 02/061119 Pamphlet and JP Patent Publication (Kokai) No. 2004-113014 A).

The 1st method involves eliminating in advance a liberated ε-glycated amino acid within a sample using an enzyme with high specificity to the ε-glycated amino acid and then determining an α-glycated amino acid alone with the use of a measurement enzyme that acts on both the α-glycated amino acid and the ε-glycated amino acid (see International Publication No. 02/061119 Pamphlet). The use of the method makes it possible to avoid partial inclusion of the measured value of an ε-glycated amino acid or an ε-glycated peptide liberated in a sample in the measured value of a target substance. However, for example, in the case of patients or the like subjected to infusion of a high-calorie amino acid solution, the method is problematic in that a liberated α-glycated amino acid that can be generated in blood during or after infusion cannot be eliminated. Specifically, such an α-glycated amino acid contaminant cannot be eliminated with the use of an enzyme for elimination. Furthermore, such an enzyme for determination is unable to distinguish between an α-glycated amino acid that has been liberated and an α-glycated amino acid that has been cleaved with protease. Therefore, the value obtained by this method includes the amount of such a liberated α-glycated amino acid that has remained uneliminated. This can cause an error.

The $2^{nd}$ method involves using an enzyme that acts on an α-glycated amino acid or an α-glycated peptide for both elimination and determination (see JP Patent Publication (Kokai) No. 2004-113014A). Specifically, a substrate on which an enzyme for determination can act is eliminated in advance from a sample before protease treatment, and then only a substrate for determination, which is newly generated by protease treatment, is determined. The α-glycated amino acid or the α-glycated peptide derived from only the subject glycated protein is thus determined. According to this method, a measurement error resulting from a contaminant that is a substrate of an enzyme for determination (=enzyme for elimination) and is in a state of being liberated before protease treatment can be avoided. However, a problem resulting from the substrate specificity of the enzyme for determination (=enzyme for elimination) still remains. With the use of this method, a model contaminant simulating an ε-glycated amino acid is successfully eliminated. Specifically, an enzyme for determination (=enzyme for elimination) in this method can act well on both an α-glycated amino acid or α-glycated peptide to be determined and an ε-glycated amino acid to be eliminated. However, a sample to be subjected to protease treatment contains a mixture of hemoglobin, blood proteins other than hemoglobin contaminated in the sample, and a plurality of proteins including protease itself. Each of these proteins contains a plurality of ε-glycated portions, so that these portions are also liberated by protease treatment, generating ε-glycated amino acids and/or ε-glycated peptides. Hence, inclusion of the measured values of such amino acids and/or peptides in the measured value of a target substance because of an enzyme for determination cannot be avoided. Therefore, it cannot be said that this method is sufficient for precise determination of an α-glycated amino acid or a glycated peptide alone.

As described above, it has been desired for enzymatic determination of a glycated protein to further improve technology relating to a method and a reagent for eliminating a glycated amino acid and/or a glycated peptide (for eliminating substances that cause measurement errors).

DISCLOSURE OF THE INVENTION

An object of the present invention is to provide a method for quantitative determination of a glycated protein used to obtain a precise measured value through reduction of measurement errors in quantitative determination of a glycated protein such as glycated hemoglobin, a reagent for eliminating substances that cause measurement errors, and a kit for quantitative determination of a glycated protein. More specifically, the object of the present invention is to provide a method for quantitative determination of a glycated protein, which comprises eliminating an α-glycated amino acid, an ε-glycated amino acid, an ε-glycated peptide, or a combination thereof in a sample to be determined and then determining an α-glycated peptide in the sample using an enzyme that acts on the α-glycated peptide, a reagent for elimination, which is used for such determination, and a kit for quantitative determination of a glycated protein.

SUMMARY OF THE INVENTION

To achieve the above object, the present inventors have conducted intensive studies concerning a method for eliminating a glycated amino acid and/or a glycated peptide that cause measurement errors in quantitative determination of glycated hemoglobin. As a result, the present inventors have discovered that measurement errors are reduced and precise measured values can be obtained in a method for quantitative determination of a glycated protein by causing protease to act on a whole blood and/or blood cell sample, causing an elimination reagent containing 1 or a plurality of types of ketoamine oxidase to act on the resultant, eliminating an α-glycated amino acid, an ε-glycated amino acid, an ε-glycated peptide, or a combination thereof, and then determining an α-glycated peptide in the sample using oxidase that acts on the α-glycated peptide.

The elimination reagent is characterized by containing 1 or a plurality of types of ketoamine oxidase, which act on an α-glycated amino acid, an ε-glycated amino acid, an ε-glycated peptide, or a combination thereof, but do not act on an α-glycated peptide, and thus eliminating the α-glycated amino acid, the ε-glycated amino acid, the ε-glycated peptide, or the combination thereof in the sample.

The present inventors have further discovered that a kit containing such elimination reagent, a reagent containing protease, and a reagent containing oxidase that acts on an α-glycated peptide enables reduction in measurement error and obtainment of precise measured values, and thus is useful in quantitative determination of a glycated protein such as glycated hemoglobin. Thus, the present inventors have completed the present invention.

The present invention relates to the following (1) to (12).

(1) A method for quantitative determination of a glycated protein, comprising causing protease to act on a whole blood and/or blood cell sample, causing an elimination reagent containing one or a plurality of types of ketoamine oxidase to act on the resultant, eliminating an α-glycated amino acid, an ε-glycated amino acid, an ε-glycated peptide, or a combination thereof, and then determining an α-glycated peptide in the sample using oxidase that acts on the α-glycated peptide.

(2) The method according to (1), wherein the ketoamine oxidase eliminates the α-glycated amino acid, the ε-glycated amino acid, and the ε-glycated peptide.

(3) The method according to (1), wherein the ketoamine oxidase is an enzyme that acts on the α-glycated amino acid but does not act on the α-glycated peptide, an enzyme that acts on the ε-glycated amino acid and/or the ε-glycated peptide but does not act on the α-glycated peptide, an enzyme that acts on the ε-glycated amino acid and/or the ε-glycated peptide and the α-glycated amino acid but does not act on the α-glycated peptide, or a combination of these enzymes.

(4) The method according to (3), wherein the enzyme that acts on the α-glycated amino acid but does not act on the α-glycated peptide is fructosyl amino acid oxidase derived from the genus *Corynebacterium, Arthrobacter*, or *Agrobacterium*.

(5) The method according to (3), wherein the enzyme that acts on the ε-glycated amino acid and/or the ε-glycated peptide but does not act on the α-glycated peptide is fructosyl amino acid oxidase derived from the genus *Fusarium* or *Gibberella*.

(6) The method according to (3), wherein the enzyme that acts on the ε-glycated amino acid and/or the ε-glycated peptide, and the α-glycated amino acid, but does not act on the α-glycated peptide is ketoamine oxidase derived from the genus *Gibberella, Fusarium, Penicillium, Aspergillus, Candida, Acremonium, Debaryomyces, Pichia, Trichosporon*, or *Bacillus*.

(7) The method according to any one of (1) to (6), wherein the oxidase that acts on the α-glycated peptide is fructosyl peptide oxidase.

(8) The method according to any one of (1) to (7), wherein the glycated protein is glycated hemoglobin.

(9) An elimination reagent, containing 1 or a plurality of types of ketoamine oxidase that act(s) on an α-glycated amino acid, an ε-glycated amino acid, an ε-glycated peptide, or a combination thereof, but does not act on an α-glycated peptide and eliminating the α-glycated amino acid, the ε-glycated amino acid, the ε-glycated peptide, or the combination thereof in a sample.

(10) The elimination reagent according to (9), wherein the ketoamine oxidase is fructosyl amino acid oxidase derived from the genus *Corynebacterium, Arthrobacter, Agrobacterium, Fusarium*, or *Gibberella*, ketoamine oxidase derived from the genus *Gibberella, Penicillium, Aspergillus, Candida, Acremonium, Debaryomyces, Pichia, Trichosporon*, or *Bacillus*, or a combination thereof.

(11) A kit for quantitative determination of a glycated protein, containing a reagent containing protease, the elimination reagent according to (9) or (10), and a reagent containing oxidase that acts on an α-glycated peptide.

(12) The kit according to (11), wherein the oxidase that acts on the α-glycated peptide is fructosyl peptide oxidase.

According to the present invention, reduction in measurement error is achieved upon quantitative determination of a glycated protein such as glycated hemoglobin and obtainment of precise measured values is realized. Moreover, an elimination reagent to be used for such quantitative determination and a kit for quantitative determination of a glycated protein such as glycated hemoglobin, which enables reduction in measurement error and obtainment of precise measured values, can be provided. They are useful in the field of clinical diagnosis.

The description shall encompass the description in the description and/or drawings of JP Patent Application No. 2005-208737, which is the basis for the priority of the present application.

DETAILED DESCRIPTION

Hereinafter, the constitutions and preferred embodiments of the invention will be further described in detail.

A glycated protein in the present invention is a non-enzymatically glycated protein. Specifically, the glycated protein is generated by nonenzymatic covalent bonding between an aldehyde group on the sugar, that is, the aldose (a monosaccharide or a derivative thereof potentially having an aldehyde group) side and an amino group on the protein side. Glycation sites in a glycated protein include an α-glycation site that is generated by glycation of the N-terminal α-amino group in a polypeptide composing a protein molecule and an ε-glycation site that is generated by glycation of an 1-amino group in the side chain of an amino acid residue within a protein molecule.

Glycated protein is contained in body fluids such as in vivo blood or biological samples such as hair. Generation of various types of glycated protein strongly depends on the concentration of sugar such as glucose in an environment where the protein is localized. For example, glycated protein generation in blood correlates with the concentration of glucose in blood, that is, a blood glucose level. Examples of such glycated protein existing in blood include glycated hemoglobin and glycoalbumin. They are used as indicators that reflect blood glucose levels in diagnosis or control of the symptoms of diabetes.

Glycated hemoglobin is further classified into several types based on the way of glycation or definition. Glycated hemoglobin particularly gaining recognition in diagnosis or control of the symptoms of diabetes is HbA1c. HbA1c is defined as a hemoglobin molecule having $\alpha_2\beta_2$ tetramer structure in which N-terminal Val (valine) is glycated in at least the "β chain." HbA1c particularly gains recognition as an indicator that reflects well a past average blood glucose level for a certain time period.

Delpierre, J. Biol. Chem., 279: 27613-20 (2004) describes residues glycataed in glycated hemoglobin. As shown in Table II of this document, in glycated hemoglobin, 16th, 61st, and 139th Lys (lysine) residues of the "α chain" and 17th, 59th, 66th, 132nd, and 144th Lys residues of the "β chain" are glycated, in addition to N-terminal Val of the "β chain." N-terminal Val of the "α chain" is almost unglycated. This may be due to the characteristic stereo-structure of a hemoglobin molecule.

In general, when glycated hemoglobin is quantitatively determined, glycation at all glycation sites described above is determined. That is, glycated amino acids and/or glycated peptides derived from all glycation sites are determined. In contrast, when HbA1c is quantitatively determined, glycation at the N-terminal Val alone of the "β chain" of the glycated hemoglobin is determined. Specifically, only the α-glycated amino acids and/or the α-glycated peptides derived from the N-terminus of the "β chain" are determined.

In addition, examples of a method for quantitative determination of HbA1c include a method for determination of an α-glycated amino acid or a method for determination of an α-glycated peptide, as described above. The method for determination of an α-glycated peptide is more preferred because of the following reasons.

First, although many proteases capable of efficiently liberating N-terminal α-glycated peptide from a glycated protein are known, proteases capable of liberating N-terminal α-glycated amino acid have not been discovered. Specifically, a substance that is liberated from the N-terminal α-glycation site of the glycated protein in a reflection of the amount of a glycated protein is practically an α-glycated peptide alone.

Second, even if protease capable of efficiently liberating an α-glycated amino acid from the N-terminal α-glycation site of a glycated protein is discovered, α-glycated amino acids are liberated from both the glycated N-terminus of the "α chain" and that of the "β chain" of glycated hemoglobin. They are indistinguishable when such α-glycated amino acids are liberated from glycated hemoglobin using such a discovered protease. Specifically, the amino acid sequence of the N-terminal $1^{st}$ residue of both the "α chain" and the "β chain" of glycated hemoglobin is Val. The α-glycated amino acid that is liberated from the "α chain" and that liberated from the "β chain" are the same; that is, fructosyl valine. Hence, it is impossible to determine glycation of the "β chain" alone.

Glycated hemoglobin is localized in erythrocytes. Hence, when glycated hemoglobin is quantitatively determined, a sample containing erythrocytes is preferably used for determination. Specifically, a whole blood and/or blood cell sample can be adequately used. Examples of the whole blood and/or blood cell samples described in the description include collected blood samples or blood for storage, commercially available standard blood (e.g., working standard substance for HbA1c determination: produced by Health Care Technology Foundation, Tokyo, Japan), samples treated by various methods, and samples supplemented with various anticoagulants and other additives.

Whole blood is a sample containing all blood components and contains erythrocytes, leukocytes, blood platelets, blood plasma, and the like as major components. A blood cell sample is a fraction prepared by separating and removing a blood plasma component from whole blood and contains erythrocytes, leukocytes, blood platelets, and the like as major components. A method for separating blood cell samples from whole blood is not particularly limited. For example, separation can be performed by centrifugation, use of a serum separation sheet (blood cell separation membrane), or the like.

When glycated hemoglobin is quantitatively determined, a whole blood and/or blood cell sample is hemolyzed and then used for determination. In general glycated hemoglobin quantitative determination, whole blood is directly hemolyzed or blood plasma is removed from whole blood by centrifugation or the like. A blood cell fraction is then separated and then hemolyzed. A hemolysis method is not particularly limited. Examples of a hemolysis method that can be employed herein include a method using a surfactant, a method using ultrasonic waves, a method using osmotic pressure differences, and a method using freezing and thawing. The thus obtained sample is subjected to each treatment for determination, including protease treatment and the like.

Meanwhile, glycoalbumin may be used as an indicator for blood sugar control over a shorter time period compared with that in the case of HbA1c. Albumin that is a protein mainly contained in serum is known to be glycated at Lys residues internally located at four positions. In a manner similar to that in the case of HbA1c quantitative determination, glycoalbumin quantitative determination also requires efficient elimination of glycated products that are contaminants in a sample and determination of only the glycated product derived from glycated Lys residues within albumin.

In the description, various oxidases (referred as various names such as fructosyl amino acid oxidase, glycated amino acid oxidase, fructosamine oxidase, and amadoriase) that act on glycated amino acids and/or glycated peptides are collectively referred as "ketoamine oxidase" or "enzyme for elimination" for convenience. According to this definition, an enzyme for determination of an α-glycated peptide, which is used as an enzyme for determination in the present invention, may also be included in the examples of ketoamine oxidase. To avoid needless confusion in terms of explanation, only this enzyme is referred to as "oxidase that acts on an α-glycated peptide" or an "enzyme for determination." In addition, the above known ketoamine oxidase enzymes actually include no enzyme having high specificity to an α-glycated peptide. Hence, the two are clearly distinguishable also in this viewpoint.

As an "enzyme for determination" in the present invention, oxidase that acts on an α-glycated peptide, such as fructosyl peptide oxidase is preferable. Examples of such enzyme include enzymes derived from the genus *Achaetomiella*, *Achaetomium*, *Thielavia*, *Chaetomium*, *Gelasinospora*, *Microascus*, *Coniochaeta*, *Eupenicillium*, *Curvularia*, *Pyrenochaeta*, or *Arthrinium* (Arch Microbiol. 180: 227-31, 2003 and JP Patent Publication (Kokai) No. 2004-275063 A). Examples of commercially available enzymes include FPOX-EE and FPOX-CE (both produced by KIKKOMAN CORPORATION, Japan). Furthermore, a genetically engineered glycated amino acid oxidase (JP Patent Publication (Kokai) No. 2001-95598 A) is also known. Fructosyl peptide oxidase activity in the present invention is determined by the method described in JP Patent Publication (Kokai) No. 2003-235585 A (novel fructosyl peptide oxidase), in which the amount of enzyme that generates 1 μmol of hydrogen peroxide for 1 minute at 37° C. is defined as 1 U.

Degree of the effect of substances that cause errors on the measured values in the method of the present invention depends also on the substrate specificity of fructosyl peptide oxidase that is an enzyme for determination. That is, the higher the substrate specificity of fructosyl peptide oxidase to be used, the easier obtainment of a precise measured value without always requiring complete elimination. Conversely, when fructosyl peptide oxidase having substrate specificity, the use of which often results in inclusion of the measured values of contaminants in that of a target substance, is used, a need of more completely eliminating various contaminants arises. For example, when fructosyl peptide oxidase, the use of which often results in inclusion of the measured value of an α-glycated amino acid in that of a target substance, is used, it is essential to eliminate the α-glycated amino acid for obtaining a precise measured value.

Moreover, more specific determination is possible by the use of fructosyl peptide oxidase having high substrate specificity (so that the enzyme is capable of distinguishing the sequences of the same α-glycated peptides) so as to be able to determine only a specific α-glycated peptide. For example, through the use of fructosyl peptide oxidase that acts on Fru-Val-His (fructosyl valyl histidine, an α-glycated peptide that can be liberated from the "β chain" side), but does not act on Fru-Val-Leu (fructosyl valyl leucine, an α-glycated peptide that can be liberated from the "α chain" side of glycated hemoglobin), only the α-glycated peptide that can be liberated from the β chain side can be determined without elimination of the α-glycated peptide that can be liberated from the "α chain" side. As such enzymes, FPOX-EE and FPOX-CE (both produced by KIKKOMAN CORPORATION, Japan) are known.

Any proteases can be used in the present invention, as long as they can be used for clinical examination and are capable of effectively cleaving at least an α-glycated peptide from a glycated protein to be determined in a sample to be treated (e.g., glycated hemoglobin). Examples of such proteases include proteases or peptidases, such as proteinase K, pronase, thermolysin, subtilisin, carboxypeptidase B, pancreatin, cathepsin, carboxypeptidase, endoproteinase Glu-C, papain, ficin, bromelain, and aminopeptidase.

Particular examples of protease that is capable of efficiently liberating an α-glycated peptide in the present invention include proteases such as: proteases derived from *Aspergillus*, such as "IP ENZYME™, AO PROTEASE, PEPTIDASE, and MOLSIN™ (all produced by KIKKOMAN CORPORATION, Japan)," "PROTEASE A5 (produced by KYOWAKASEI CO.,LTD., Japan)," "UMAMIZYME, PROTEASE A, PROTEASE M, PROTEASE P, and PEPTIDASE R (all produced by Amano Enzyme Inc., Japan)," "SUMIZYME MP™, SUMIZYME LP-20™, SUMIZYME LPL™, and SUMIZYME AP™ (all produced by Shin Nihon Chemical Co. Ltd., Japan)," and "PROTEINASE 6 (produced by Fluka, U.S.A.)"; enzymes derived from *Rhizopas*, such as "PEPTIDASE R (produced by Amano Enzyme Inc., Japan); proteases derived from *Bacillus*, such as "DISPASE (produced by Roche, Swiss)," "SUBTILISIN (produced by Boehringer Mannheim Corporation, Germany)," "PROTEINASE N (produced by Fluka, U.S.A.)," "PROTEINASE Type VII (produced by Sigma-Aldrich Corporation, U.S.A.)," "PROTEINASE (Bacterial) (produced by Fluka, U.S.A.)," "PROTEASE N, PROLEATHER FG-F™, and PROTEASE S (all produced by Amano Enzyme Inc., Japan)," "PROTEINASE Type X (produced by Sigma-Aldrich Corporation, U.S.A.)," "thermolysin (produced by DAIWA KASEI K.K., Japan)," "PRONASE E (produced by Kaken Pharmaceutical Co., Ltd., Japan)," and "neutral protease (produced by TOYOBO., LTD., Japan)"; proteases derived from *Streptomyces*, such as "PRONASE (produced by Boehringer Mannheim Corporation, Germany)," "PROTEINASE Type XIV (produced by Sigma-Aldrich Corporation, U.S.A.)," and "alkaline protease (produced by TOYOBO., LTD., Japan)"; protease derived from *Tritirachium*, such as "PROTEINASE K (produced by Roche, Swiss and Wako Pure Chemical Industries, Ltd., Japan)"; protease derived from *Staphylococcus*, such as "Glu-C™ (produced by Boehringer Mannheim Corporation, Germany)"; proteases derived from plants, such as papain (produced by Roche, Swiss, Wako Pure Chemical Industries, Ltd., Japan, Sigma-Aldrich Corporation, U.S.A., Amano Enzyme Inc., Japan, and ASAHI FOOD & HEALTH- CARE, LTD., Japan)," "ficin (produced by Sigma-Aldrich Corporation, U.S.A.)," "bromelain (produced by Amano Enzyme Inc., Japan and Sigma-Aldrich Corporation, U.S.A.)"; and proteases derived from animals, such as "pancreatin (produced by Wako Pure Chemical Industries, Ltd., Japan)" and "cathepsin B (produced by Sigma-Aldrich Corporation, U.S.A.). Samples containing these proteases are particularly preferably used.

The above proteases may be used independently or 2 or more types thereof may be used in combination. For example, regarding glycated hemoglobin, it is known that α-glycated hexapeptide (fructosyl Val-His-Leu-Thr-Pro-Glu, SEQ ID NO. 1) is generated by endoproteinase Glu-C (Kobold U., et al, Clin. Chem. 1997, 43: 1944-1951). Accordingly, combining Glu-C with the above protease is an extremely effective method for producing an .alpha.-glycated peptide from glycated hemoglobin. In addition, the above groups of proteases are merely specific examples and the examples are not limited thereto.

When protease is selected in the present invention, the enzyme can also be selected in terms of efficient cleavage of an α-glycated peptide from a glycated protein to be determined and suppression of generation of contaminants as far as possible. Specifically, glycated amino acids and/or peptides derived from glycated proteins (contained in a determination sample) other than the glycated protein to be determined are predicted as contaminants, so that a type of protease that hardly results in generation of such contaminants is selected. Thus, generation of contaminants can be suppressed. There have been numerous findings about which linkage between amino acid residues various known proteases tend to cleave. Protease can be selected based on such information.

Protease treatment conditions for a sample may be any conditions, as long as they are conditions under which protease to be used herein can act on glycated hemoglobin, following which an α-glycated peptide can be efficiently liberated within a short time period. The amount of protease to be used herein is appropriately selected depending on the content of glycated hemoglobin contained in a sample, treatment conditions, or the like. In an example, protease derived from the members of the genus *Aspergillus* (e.g., protease P marketed by Amano Enzyme Inc., Japan) is added at a final concentration between 0.1 U/mL and 50 U/mL and preferably 1 U/mL and 10 U/mL. Furthermore, other proteases may also be appropriately added, if necessary.

pH employed upon protease treatment may be non-adjusted pH. Alternatively, to achieve appropriate pH for the action of protease to be used, pH may be adjusted using an appropriate pH adjuster such as hydrochloric acid, acetic acid, sulfuric acid, sodium hydroxide, or potassium hydroxide to pH 2 to pH 9 and preferably pH 3 to pH 8, for example. Treatment may also be carried out within a temperature range between 20° C. and 50° C., for example. Depending on an enzyme to be used, treatment may also be carried out within a higher temperature range between 45° C. and 70° C. Treatment time to be employed herein may be any treatment time sufficient for denaturation of glycated protein. Specifically, treatment may be carried out for 30 seconds to 180 minutes and preferably 1 to 60 minutes. The thus obtained treatment solution may be directly used or indirectly used after appropriate heating, centrifugation, condensation, dilution, or the like, if necessary.

The activity of protease that can be used in the present invention is determined by the Casein-Folin method. Color development obtained by the use of 1 µg of tyrosine at 37° C. for 1 minute is defined as 1 U.

Glycated amino acids and/or glycated peptides to be eliminated in the present invention include not only liberated glycated amino acids and/or glycated peptides contained in blood, blood plasma, serum, and the like, but also glycated amino acids and/or glycated peptides derived from hemoglobin and glycated proteins other than hemoglobin, which are generated simultaneously with the generation of a glycated amino acid and/or a glycated peptide to be determined via protease treatment. Specifically, when glycated hemoglobin is quantitatively determined, only an α-glycated peptide that is cleaved by protease treatment of glycated hemoglobin is a subject for determination. However, glycated amino acids and/or glycated peptides derived from glycated proteins other than hemoglobin and a glycated-hemoglobin-derived ε-glycated amino acid, ε-glycated peptide, and α-glycated amino acid can cause errors.

Specifically, a substance that should be determined in this system is only an α-glycated peptide derived from glycated hemoglobin. In contrast, contaminants that should be eliminated herein are: a liberated α-glycated amino acid, α-glycated peptide, ε-glycated amino acid, and ε-glycated peptide; an α-glycated amino acid, an α-glycated peptide, an ε-glycated amino acid, and an ε-glycated peptide derived from glycated proteins other than hemoglobin; and an ε-glycated amino acid, an ε-glycated peptide, and an α-glycated amino acid derived from glycated hemoglobin.

Moreover, there are 2 types of α-glycated peptide derived from hemoglobin, which are the above substances to be determined. This is because a hemoglobin molecule is composed of different types of subunit, the "α chain" and the "β chain." They differ in terms of N-terminal amino acid sequence. Furthermore, this is because α-glycated peptides having different structures are generated depending on the subunit type ("α chain" or "β chain") within the hemoglobin molecule from which the peptide is liberated. Regardless of the origin of the peptide (that is, whether the peptide is derived from the "α chain" or the "β chain"), when the sum of the amounts of α-glycated peptides is measured, there is no need to distinguish between the two. On the other hand, when only the amount of an α-glycated peptide derived from a specific subunit is intended to be measured, an α-glycated peptide derived from the other subunit is also regarded as a contaminant. For example, when HbA1c is quantitatively determined, an α-glycated peptide that is liberated from the "β chain" of hemoglobin is determined. Hence, an α-glycated peptide derived from the "α chain" can principally be a contaminant that can cause an error. Hereinafter, elimination of various contaminants or the effects of contaminants that cannot be eliminated on the measured values of the present invention will be described in order as follows.

First, various contaminants that can be eliminated with the use of ketoamine oxidase will be described as follows. When an α-glycated peptide is determined using fructosyl peptide oxidase that is an enzyme for determination, for example, if the substrate specificity of fructosyl peptide oxidase is extremely high so that the enzyme does not actually act on a contaminant such as an α-glycated amino acid, an ε-glycated amino acid, or an ε-glycated peptide, elimination of these amino acids is naturally unnecessary. However, various known fructosyl peptide oxidases somewhat act on contaminants in greater or less degrees. In particular, such known fructosyl peptide oxidases tend to act on α-glycated amino acids with high constitutional similarity. Therefore, in the present invention, elimination of an α-glycated amino acid is particularly important to realize precise quantitative determination. With a conventional assay system using ketoamine oxidase, it is impossible to perform determination while focusing on distinguishing between an α-glycated peptide and an α-glycated amino acid. According to the present invention, it becomes possible to eliminate an α-glycated amino acid and to determine only an α-glycated peptide through the use of various ketoamine oxidases for elimination and fructosyl peptide oxidase for determination. Hence, efficient elimination is realized according to the present invention.

To further reduce measurement errors, an ε-glycated amino acid and/or an ε-glycated peptide can be eliminated again in the present invention. Any additional elimination may not be performed naturally when additional elimination is not required because of the characteristics of a sample or the substrate specificity of an enzyme for determination. Moreover, with the use of the substrate specificity of an enzyme for elimination, a plurality of substances can also be eliminated simultaneously with the same enzyme. Alternatively, a plurality of substances may also be eliminated by the action of each enzyme exerted with the use of a plurality of enzymes in combination. For example, an ε-glycated amino acid and an ε-glycated peptide tend to be eliminated together by a specific type of enzyme.

Next, contaminants that cannot be eliminated with ketoamine oxidase are described as follows. Specifically, such contaminants are α-glycated peptides and more specifically liberated α-glycated peptides, α-glycated peptides derived from glycated proteins other than hemoglobin, or α-glycated peptides derived from the "α chain" of hemoglobin when HbA1c is quantitatively determined. They cannot be eliminated by ketoamine oxidase that is an enzyme for elimination, so that they may remain uneliminated in the assay system. However, they unlikely have significant effects on measured values in the assay system of a glycated protein, which is an object of the present invention and particularly in the assay system of glycated hemoglobin. Possible reasons for this are as follows.

First, most liberated contaminants that are likely increased by the effect of an infusion solution or the like are glycated amino acids. Hence, the amount of a liberated glycated peptide is unlikely increased. This is because not peptides but amino acids are contained rich in an infusion solution.

Second, in principle, only one α-glycated peptide (that is liberated via protease treatment of a glycated protein) can be generated at maximum from the N terminus of each polypeptide composing the glycated protein. Compared with an ε-glycated peptide that may be liberated in a large amount when a glycated protein contains a plurality of ε-glycation sites therewithin, the absolute amount of such α-glycated peptide that can contaminate is low.

Third, in HbA1c, contamination with an α-glycated peptide derived from the "α chain" of hemoglobin almost never takes place physically. Table II in Delpierre, J. Biol. Chem., 279: 27613-20 (2004) shows the relative amount of each glycated site in glycated hemoglobin, in which the amount of α-glycation on the N-terminus of the "β chain" is the highest and the relative amount thereof is 0.32. Moreover, the total relative amount of ε-glycation within the "α chain" is approximately 0.4 and the total relative amount of ε-glycation within the "β chain" is 0.22. In contrast, the relative amount of α-glycation on the N-terminus of the "α chain" is only 0.01. Therefore, contamination with an α-glycated peptide derived from the "α chain" of hemoglobin is never be a substantial problem. In the quantitative determination method of the present invention, an α-glycated peptide remaining as an uneliminated contaminant does not actually adversely affect measured values.

If contamination with particularly a large amount of a liberated α-glycated peptide can take place, in such a case, the α-glycated peptide is eliminated with the use of fructosyl peptide oxidase before protease treatment. Hence, only an α-glycated peptide that is newly liberated after protease treatment can be calculated. Moreover, as described above concerning protease selection, protease having substrate specificity, by which contaminant generation is suppressed as far as possible, is selected, so that generation of an α-glycated peptide as a contaminant can be sufficiently suppressed.

In addition, as described above concerning fructosyl peptide oxidase selection, with the use of fructosyl peptide oxidase that does not act on Fru-Val-Leu (fructosyl valyl leucine, which is an α-glycated peptide that can be liberated from the "α chain" side of glycated hemoglobin), but acts on Fru-Val-His (fructosyl valyl histidine, which is an α-glycated peptide that can be liberated from the "β chain" side), for example, a precise measured value not including the amount of contaminants that are present because of an enzyme for determination can be obtained.

As an "enzyme for elimination" of the present invention, any enzyme can be used, as long as it is ketoamine oxidase acting well on a glycated amino acid and/or a glycated peptide to generate hydrogen peroxide. "Ketoamine oxidase acting on an ε-glycated amino acid and/or an ε-glycated peptide," "ketoamine oxidase acting on an α-glycated amino acid," and/or "ketoamine oxidase acting on an ε-glycated amino acid and/or an ε-glycated peptide and an α-glycated amino acid" are preferred.

As examples of "ketoamine oxidase having high specificity to an ε-glycated amino acid and/or an ε-glycated peptide," an enzyme derived from the genus *Gibberella* and an enzyme derived from the genus *Fusarium* are known. Specific examples of such enzymes include fructosyl lysineoxidase (derived from the genus *Fusarium* or *Gibberella*, see JP Patent Publication (Kokai) No. 11-243950 A (1999)), ketoamine oxidase (derived from the genus *Fusarium*, marketed by Genzyme Corporation (U.S.A.)), and fructosamine oxidase (produced by Asahi Kasei Corporation (Japan), see PCT/JP02/00721). These enzymes are characteristic in that they do not substantially act on an α-glycated amino acid.

Moreover as examples of "ketoamine oxidase having high specificity to an α-glycated amino acid," an enzyme derived from the genus *Corynebacterium*, an enzyme derived from the genus *Agrobacterium*, and an enzyme derived from the genus *Arthrobacter* are known. Other examples of the same include FAOX-C (derived from *Corynebacterium*, Bisci Biotechnol Biochem., See 66:1256-61, 2002), FAOX-TE (derived from *Corynebacterium*, produced by KIKKOMAN CORPORATION (Japan)), fructosyl amino acid oxidase (derived from the genus *Corynebacterium*, produced by Sigma-Aldrich Corp. (U.S.A.)), AgaE-like Protein (derived from the genus *Agrobacterium*, see Biosci Biotechnol Biochem. 66: 2323-9, 2002), and ArFAOD (derived from the genus *Arthrobacter*, see Biotechnol Lett. 27: 27-32, 2005). These enzymes are characteristic in that they do not substantially act on an ε-glycated amino acid and an ε-glycated peptide.

Furthermore, as examples of "ketoamine oxidase acting on an ε-glycated amino acid and/or an ε-glycated peptide, and an α-glycated amino acid," an enzyme derived from the genus *Gibberella*, an enzyme derived from the genus *Fusarium*, an enzyme derived from the genus *Penicillium*, an enzyme derived from the genus *Aspergillus*, an enzyme derived from the genus *Candida*, an enzyme derived from the genus *Acremonium*, an enzyme derived from the genus *Debaryomyces*, an enzyme derived from the genus *Pichia*, an enzyme derived from the genus *Trichosporon*, and an enzyme derived from the genus *Bacillus*, are known. Specific examples of the same include fructosyl amino acid oxidase (derived from the genus Fusarium, see JP Patent Publication (Kokai) No. 8-154672 A (1996)), fructosyl amino acid oxidase (derived from the genus *Penicillium* or *Aspergillus terreus*, see Eur J. Biochem. 242: 499-505, 1996), fructosyl amine oxidase (derived from the genus *Aspergillus*, see Agric biol chem 55: 333-8, 1991), amadoriase I, II (derived from *Aspergillus fumigatus*, see J Biol. Chem. 272: 3437-43 1997), fructosyl amino acid oxidase (derived from the genus *Aspergillus*, produced by Diazyme Laboratories (U.S.A.)), fructosyl amino acid oxidase (derived from *Aspergillus nidulans*, see Arch Microbiol. 178: 344-50, 2002), fructosyl amino acid oxidase (derived from *Aspergillus oryzae*, see Appl Environ Microbiol. 70: 5882-90, 2004), fructosyl amine deglycase (derived from the genus *Candida*, see U.S. Pat. No. 5,387,109), ketoamine oxidase (derived from the genus *Acremonium* or the genus *Debaryomyces*, see U.S. Pat. No. 5,370,990), fructosyl amine oxidase (derived from the genus *Pichia*, see Mar Biotechnol 6: 625-32, 2004), fructosyl amino acid oxidase (derived from the genus *Trichosporon*, see JP Patent Publication (Kokai) No. 2000-245454 A), fructosyl amine oxidase (derived from the genus *Bacillus*, see JP Patent Publication (Kokai) No. 2002-125663 A), ketoamine oxidase (produced by Asahi Kasei Corporation (Japan), see JP Patent Publication (Kokai) No. 2004-222570 A), and FAOD-E (see KIKKOMAN CORPORATION (Japan)).

In addition, all of these ketoamine oxidases described above including these enzymes do not act on α-glycated peptides. Therefore, elimination is performed using these enzymes in arbitrary combination, so that contaminants can be efficiently eliminated without eliminating a target α-glycated peptide. Elimination of all amino acid types including an α-glycated amino acid, an ε-glycated amino acid, and an ε-glycated peptide through the use of a combination of a plurality of enzymes is the most preferable, because the contaminants can be eliminated more completely.

Ketoamine oxidase activity is determined by the method described in JP Patent Publication (Kokai) No. 11-155579 A (1999) (Method for producing fructosyl amino acid oxidase gene, novel recombinant DNA, and fructosyl amino acid oxidase). The amount of enzyme that generates 1 μmol of hydrogen peroxide for 1 minute at 37° C. is defined as 1 U.

The "enzyme for elimination" of the present invention may be added at a final concentration ranging from 0.1 U/mL to 50 U/mL and preferably ranging from 1 U/mL to 10 U/mL depending on the amount of a glycated amino acid and/or a glycated peptide contained in a treatment solution, for example. The enzyme is caused to act at pH ranging from pH3 to pH11 and particularly preferably ranging from pH5 to pH9, for example. It is preferable to adjust pH using a buffer agent so as to achieve a pH appropriate for reaction in view of the optimum pH for ketoamine oxidase. However, the pH is not limited to such pH, as long as the pH enables such oxidase to act. The method for adjusting pH is not particularly limited. Examples of such buffer agent include N-[tris(hydroxymethyl)methyl]glycine, phosphate, acetate, carbonate, tris(hydroxymethyl)-aminomethane, borate, citrate, dimethyl glutamate, tricine, and HEPES. Furthermore, if necessary, the pH of a reaction solution may also be appropriately adjusted at the above pH using a buffer agent.

Action time ranges from 1 to 120 minutes and preferably 1 to 30 minutes, for example, depending on the amount of a glycated amino acid and/or a glycated peptide to be used as a substrate. Any action time may be employed, as long as it is sufficient for ketoamine oxidase to act on such a peptide. Action temperature ranges from 20° C. to 45° C., for example. Temperature employed for a general enzyme reaction can be appropriately selected.

The amount of hydrogen peroxide generated by the action of ketoamine oxidase may also be degraded by catalase or the like. Examples of a buffer agent to be used in the present invention include N-[tris(hydroxymethyl)methyl]glycine, phosphate, acetate, carbonate, tris(hydroxymethyl)-aminomethane, borate, citrate, dimethyl glutamate, tricine, and HEPES. Furthermore, if necessary, within a range that does not deteriorate the purpose of the present invention, various additives including a solubilizing agent, a stabilizing agent, a surfactant (e.g., triton X-100, bridge 35, Tween 80, or cholate), a reducing agent (e.g., dithiothreitol, mercaptoethanol, or L-cysteine), bovine serum albumin, saccharides (e.g., glycerine, lactose, or sucrose), and the like may be appropriately added.

After protease treatment of a sample containing glycated hemoglobin, substances that cause errors are eliminated through the use of an "enzyme for elimination" of the present invention. It is important to perform this elimination after protease treatment. When the present inventors have actually performed elimination before protease treatment, quantitatively precise determination cannot be performed. In contrast, the present invention is characterized by performing such elimination by causing one or more types of ketoamine oxidase to act on a sample after protease treatment.

An enzyme for elimination of an α-glycated amino acid, an enzyme for elimination of an ε-glycated amino acid and/or an ε-glycated peptide, or any combination of these enzymes may be used herein. It is desired that a liberated α-glycated amino acid, ε-glycated amino acid, and ε-glycated peptide are eliminated from and an α-glycated peptide remains in a sample after treatment. For this purpose, a combined use of "ketoamine oxidase acting on a glycated amino acid with glycated α-amino group" and "ketoamine oxidase acting on a glycated amino acid and/or peptide with a glycated ε-amino group is desired. Moreover, it is desired that ketoamine oxidase does not act on an α-glycated peptide. When it is clear that substances to be eliminated are present in particularly large amounts before protease treatment, another elimination step can further be introduced before protease treatment.

When an enzyme for elimination is caused to act after protease treatment, reaction conditions can be designed to prevent protease from degrading rapidly an enzyme for elimination. For example, conditions in which an enzyme for elimination is not easily degraded by protease can be determined in view of differences in optimum pH for reaction or appropriate action temperature between protease and an enzyme for elimination and the effects of salts, metals, chelating agents, or protease inhibitors on the activity of each enzyme, for example. Furthermore, a method that can also be used herein involves adjusting quantitative balance between the two enzymes through dilution of a treatment solution, the addition of a large amount of an enzyme for elimination, or the like. Alternatively, protease can be physically removed by a method such as membrane filtration, chromatography, or salting-out. Alternatively, protease can be inactivated by heat treatment, acid-alkali treatment, dilution, or the like. When an enzyme for elimination is degraded by protease without adversely affecting the measured value, determination of special conditions is not required.

The method of the present invention further comprises measuring the amount of an α-glycated peptide using oxidase that acts on the α-glycated peptide after elimination of substances to be eliminated. For example, after elimination, fructosyl peptide oxidase such as FPOX that is an "enzyme for determination" is caused to act on a sample, so that the amount of the α-glycated peptide can be precisely measured.

Fructosyl peptide oxidase to be used herein may be added at a final concentration ranging from 0.1 U/mL to 50 U/mL and preferably ranging from 1 U/mL to 10 U/mL, for example, depending on the amount of an α-glycated peptide contained in the treatment solution. The enzyme is caused to act at pH ranging from pH3 to pH11 and particularly preferably ranging from pH5 to pH9, for example. It is preferable to adjust pH using a buffer agent so as to achieve a pH appropriate for determination in view of the optimum pH for fructosyl peptide oxidase. However, the pH is not limited to such pH, as long as the pH enables such oxidase to act. The method for adjusting pH is not particularly limited. Examples of such buffer agent include N-[tris(hydroxymethyl)methyl]glycine, phosphate, acetate, carbonate, tris (hydroxymethyl)-aminomethane, borate, citrate, dimethyl glutamate, tricine, and HEPES. Furthermore, if necessary, the pH of a post-protease-treatment solution may also be appropriately adjusted at the above pH using a buffer agent. Action time ranges from 1 to 120 minutes and preferably 1 to 30 minutes, for example, depending on the amount of a glycated peptide to be used as a substrate. Any action time may be employed, as long as it is sufficient for fructosyl peptide oxidase to act on such a peptide. Action temperature ranges from 20° C. to 45° C., for example. Temperature employed for a general enzyme reaction can be appropriately selected.

Hydrogen peroxide generated by the action of fructosyl peptide oxidase may also be determined by any method. Examples of such methods include an electric method using oxygen electrodes, and preferably, an enzymatic method using peroxidase and a proper chromogenic substrate. For example, in the present invention, it is preferable to carry out determination using an enzymatic method with simple procedures within a short time period. An example of a reagent for determination of hydrogen peroxide by an enzymatic method is composed of a 5 mM to 500 mM and preferably 50 mM to 100 mM buffer agent (preferably pH 4 to pH 10), 0.01 mM to 50 mM and preferably 0.1 mM to 20 mM 4-aminoantipyrine as a chromogenic substrate, 0.1 U/mL to 50 U/mL and preferably 1 U/mL to 20 U/mL peroxidase, and the like. Examples of such buffer agent to be used for an assay system include N-[tris (hydroxymethyl)methyl]glycine, phosphate, acetate, carbonate, tris(hydroxymethyl)-aminomethane, borate, citrate, dimethyl glutamate, tricine, and HEPES.

Examples of a chromogenic substrate include, in addition to 4-aminoantipyrine, ADOS(N-ethyl-N-(2-hydroxy-3-sulfopropyl)-m-anisidine), ALOS(N-ethyl-N-(2-hydroxy-3-sulfopropyl)aniline), DA-67 (10-(carboxymethyl-aminocarbonyl)-3,7-bis (dimethylamino)phenothiazine), and DA-64 (N-(carboxymethyl-aminocarbonyl)-4,4'-bis (dimethylamino)diphenylamine).

Furthermore, if necessary, various additives including a solubilizing agent or a stabilizing agent, such as a surfactant (e.g., triton X-100, bridge 35, Tween 80, or cholate), a reducing agent (e.g., dithiothreitol, mercaptoethanol, or L-cysteine), bovine serum albumin, saccharides (e.g., glycerine, lactose, or sucrose), and the like, may be appropriately added.

When hydrogen peroxide is determined, in general, it is preferable to simultaneously carry out a step of generating hydrogen peroxide through the action of oxidase. In the present invention, a fructosyl peptide oxidase is preferably added at 0.1 U/mL to 50 U/mL and preferably 1 U/mL to 10 U/mL, for example, to the above reagent for determination of hydrogen peroxide. These reagents for determination may be used in a dry form or in a state of being dissolved or may also be used in the form of a carrier on a thin film such as paper (e.g., an impregnatable sheet of paper) impregnated with such reagent.

Enzymes used in the reagents for determination can also be immobilized by a standard method and then repeatedly used. The temperature for determination ranges from 20° C. to 45° C., for example. Such temperature can be appropriately selected from temperatures that are used for general enzyme reactions. The time required for determination can be appropriately selected depending on various determination conditions. For example, such time for determination may range from 0.1 to 60 minutes and particularly preferably 1 to 10 minutes. The degree of color development (the amount of change in absorbance) of the above reagent for determination is measured using a spectrophotometer. The result is compared with a standard absorbance. Thus, a glycated peptide or a glycated protein contained in a sample can be determined. A general autoanalyser can also be used for determination.

The present invention further provides an elimination reagent, which is characterized by containing one or a plurality of types of ketoamine oxidase that acts on an α-glycated amino acid, an ε-glycated amino acid, an ε-glycated peptide, or a combination thereof, but do not act on an α-glycated peptide and eliminating such an α-glycated amino acid, ε-glycated amino acid, ε-glycated peptide, or combination thereof in a sample.

Through combination of ketoamine oxidases that are used for elimination in the present invention, an elimination reagent can be prepared. A plurality of target substances to be eliminated can be efficiently eliminated simultaneously through the use of the elimination reagent. This elimination reagent may contain one or more types of ketoamine oxidase described above differing in substrate specificity in addition to various ingredients such as a stabilizing agent, a buffer agent, and other ingredients that improve elimination efficiency and thus contribute to enzyme stabilization.

Specific examples of ketoamine oxidase include enzymes listed in the specific examples of such an "enzyme for elimination" above, such as fructosyl lysine oxidase (derived from the genus *Fusarium* or *Gibberella*), ketoamine oxidase (derived from the genus *Fusarium* and marketed by Genzyme Corporation (U.S.A.)), fructosamine oxidase (produced by Asahi Kasei Corporation (Japan)), FAOX-C (derived from *Corynebacterium*), FAOX-TE (derived from *Corynebacterium* and marketed by KIKKOMAN CORPORATION (Japan)), fructosyl amino acid oxidase (derived from the genus *Corynebacterium* and marketed by Sigma-Aldrich Corp. (U.S.A.)), AgaE-like Protein (derived from the genus *Agrobacterium*), ArFAOD (derived from *Arthrobacter*), fructosyl amino acid oxidase (derived from the genus *Penicillium* and derived from *Aspergillus terreus*), fructosyl amine oxidase (derived from the genus *Aspergillus*), amadoriase I, II (derived from *Aspergillus fumigatus*), fructosyl amino acid oxidase (derived from the genus *Aspergillus* and marketed by Diazyme Laboratories (U.S.A.)), fructosyl amino acid oxidase (derived from *Aspergillus nidulans*), fructosyl amino acid oxidase (derived from *Aspergillus oryzae*), fructosylamine deglycase (derived from the genus *Candida*), ketoamine oxidase (derived from genus *Acremonium* or *Debaryomyces*), fructosyl amine oxidase (derived from the genus *Pichia*), fructosyl amino acid oxidase (derived from the genus *Trichosporon*), fructosyl amine oxidase (derived from the genus *Bacillus*), ketoamine oxidase (produced by Asahi Kasei Corporation (Japan)), FAOD-E (produced by KIKKOMAN CORPORATION (Japan)), and combinations thereof.

Furthermore, the present invention provides a kit for quantitative determination of a glycated protein such as glycated hemoglobin, containing the above elimination reagent, a protease-containing reagent for protease treatment, and a reagent containing oxidase (for determination) that acts on an α-glycated peptide. The kit for quantitative determination of a glycated protein such as glycated hemoglobin of the present invention may be prepared to contain each of the above reagents in different containers. For example, such kit can be provided as a liquid product, a frozen liquid product, or a freeze-dried product.

Oxidase that acts on an α-glycated peptide, which is preferably used in the present invention is fructosyl peptide oxidase.

An enzyme reaction reagent for quantification of glycated hemoglobin based on the present invention can be supplemented with adequately selected various known ingredients, such as a surfactant, a salt, a buffer agent, a pH adjuster, and an antiseptic agent.

Moreover, the quantitative determination method, the elimination reagent, and the kit of the present invention may also be applied to systems for quantification or the like of hydrogen peroxide using an electrode and the like.

Specifically, the titer of fructosyl peptide oxidase that acts on an α-glycated dipeptide can be determined by the following method, for example. Such titer can also be determined by other methods.

(1) Preparation of Reagent

Reagent 1 (R1): 1.0 kU of peroxidase (hereinafter abbreviated as POD, produced by KIKKOMAN CORPORATION (Japan)) and 100 mg of 4-aminoantipyrine (hereinafter abbreviated as 4AA, produced by Tokyo Kasei Kogyo Co., Ltd. (Japan)) are dissolved in a 0.1 M potassium phosphate buffer (pH 8.0). The resulting solution is prepared to a constant volume of 1 L.

Reagent 2 (R2): 500 mg of TOOS (N-ethyl-N-(2-hydroxy-3-sulfopropyl)-m-toluidine, produced by DOJINDO LABORATORIES (Japan)) is dissolved in ion exchange water. The resulting solution is prepared to a constant volume of 100 mL.

Reagent 3 (R3): 1.25 g of fructosyl Val-His (MW416, see JP Patent Publication (Kokai) No. 2003-235585 A concerning the production method) is dissolved in ion exchange water. The resulting solution is prepared to a constant volume of 10 mL.

(2) Determination

100 μL of R2 is added to 2.7 mL of R1. 100 μL of an enzyme solution containing fructosyl peptide oxidase is further added to and mixed well with the solution, followed by 5 minutes of pre-heating at 37° C.

Subsequently, 100 μL of R3 is added to and mixed well with the solution. A change in absorbance at 555 nm (difference between absorbance determined before and the same determined after 5 minutes of reaction at 37° C.) is determined using a spectrophotometer (U-2000A, produced by Hitachi, Ltd. (Japan)). In addition, the similar procedures are carried out for a control solution, except that 100 μL of ion exchange water is added instead of 100 μL of R3. A graph is obtained by plotting absorbances reflecting the amounts of pigment generated at various concentrations of the previously prepared standard solutions of hydrogen peroxide. Based on such graph, the amounts of hydrogen peroxide corresponding to changes in absorbance are found. These numerical values are used as activity units in enzyme solutions. The amount of enzyme that generates 1 μmol of hydrogen peroxide for 1 minute is determined to be 1 U.

EXAMPLES

Examples of the present invention will be described in detail as follows, but the scope of the present invention is not limited by these Examples.

Example 1

<Test for Elimination of Contaminant in HbA1c Quantitative Determination>

Hemoglobin A1c (HbA1c) was used as a glycated protein to be determined herein. The effect of the present invention of eliminating contaminants was verified by an HbA1c quantitative determination test using systems for determination of an α-glycated peptide generated by protease treatment with the use of FPOX. Specifically, the model systems used herein were prepared by artificially adding various contaminants thought to be generated via liberation or protease treatment.

(1) Glycated protein to be determined: Working standard substance for HbA1c determination (produced by HECTEF Standard Reference Center Foundation (Japan)) 130 g/L (HbA1c value: 5.8%)

(2) Added contaminants: Fru-Val (fructosyl valine, α-glycated amino acid), Fru-Gly (fructosyl glycine, α-glycated amino acid), ε-Fru-Lys (E-fructosyl lysine, ε-glycated amino acid), Fru-Val-Leu (corresponding to fructosyl valyl leucine, α-glycated peptide, or α-glycated dipeptide liberated from the N-terminus of the "α chain" of glycated hemoglobin)

(3) Preparation of HbA1c Containing Contaminant Added Thereto

HbA1c (in (1)) samples were used in 6 groups. Fru-Val was added to a sample of the $1^{st}$ group, Fru-Gly was added to a sample of the $2^{nd}$ group, ε-Fru-Lys was added to a sample of the $3^{rd}$ group, and Fru-Val-Leu was added to a sample of the $4^{th}$ group, at a concentration of 250 μM in each sample. All contaminants were added to a sample of the $5^{th}$ group at a concentration of 250 μM (concentration per contaminant) in the sample. These contaminants added were regarded as liberated contaminants or measurement-error-causing contaminants generated by protease treatment. The contaminants were subjected to determination including the following elimination treatment. A normal saline solution was added to a sample of the $6^{th}$ group instead of a contaminant, so as to prepare a sample containing no additives.

(4) Preparation of Reagent

Reagents to be used for determination were prepared with compositions listed in Table 1.

TABLE 1

Composition of reagent for determination

A. Protease-containing reagent

| | |
|---|---|
| 250 mM | CHES buffer (produced by Wako Pure Chemical Industries, Ltd.) pH 9.0 |
| 1.0 U/ml | Protease derived from *Bacillus* (produced by Roche) |

B. Elimination reagent 1

| | |
|---|---|
| 20 mM | MOPS buffer (produced by DOJINDO Laboratories) pH 7.5 |
| 50 mM | Sodium chloride (produced by Wako Pure Chemical Industries, Ltd.) |
| 250 U/ml | Catalase (produced by KIKKOMAN CORPORATION) |
| 8.0 U/ml | Ketoamine oxidase (hereinafter, FAOX-TE, produced by KIKKOMAN CORPORATION) |
| 8.0 U/ml | Ketoamine oxidase (hereinafter FAOD-E, produced by KIKKOMAN CORPORATION) |
| 5.0 mM | EDTA2 sodium (produced by DOJINDO Laboratories) |
| 0.2% | BT-7 (Nikko Chemicals Co., Ltd.) |
| 0.3% | BT-9 (Nikko Chemicals Co., Ltd.) |

C. Reagent for determination

| | |
|---|---|
| 300 mM | TES buffer (produced by DOJINDO Laboratories) pH 8.0 |
| 0.15 mM | DA-64 (produced by Wako Pure Chemical Industries, Ltd.) |
| 24 U/ml | Fructosyl peptide oxidase (FPOX-CE, produced by KIKKOMAN CORPORATION) |
| 15 U/ml | POD (produced by KIKKOMAN CORPORATION) |
| 0.15% | Sodium azide (produced by Wako Pure Chemical Industries, Ltd.) |

The elimination reagent 1 of B contains two different types of ketoamine oxidase differing in substrate specificity. FAOX-TE is a type of ketoamine oxidase having high specificity to an α-glycated amino acid. FAOD-E is a type of ketoamine oxidase having high specificity to an ε-glycated amino acid and an ε-glycated peptide. Moreover, among ketoamine oxidases, elimination reagent 2 containing FAOX alone and elimination reagent 3 containing FAOD alone were prepared as the elimination reagents of the present invention.

(5) Determination Method

20 µl of each sample prepared in (3) was mixed with 40 µl of a lysing agent (SULFOLYSER: produced by SYSMEX Corporation, Japan) and 40 µl of purified water, thereby preparing a hemolysis sample. Subsequently, 10 µl each of the hemolysis sample was mixed with 30 µl of the protease-containing reagent of A, followed by 90 minutes of protease treatment at 37° C. 40 µl of a post treatment sample was mixed with 220 µl of the elimination reagent of B, followed by 5 minutes of reaction at 37° C. Absorbance at 750 nm was measured ($A_0$). 100 µl of the reagent for determination of C was added, incubation was performed at 37° C. for 5 minutes, and then absorbance at 750 nm was measured ($A_1$). Furthermore, a change in absorbance of a blank sample using a system using a normal saline solution instead of a sample (blank $\Delta A = A_1$ blank $- A_0$ blank) was measured. Furthermore, with the use of a specimen with a known concentration, a change in absorbance of the specimen was obtained by subtracting a change in absorbance of the blank sample (($A_1 - A_0$)–blank $\Delta A$). The concentration of glycated hemoglobin was thus calculated. The glycated hemoglobin concentration was divided by the hemoglobin concentration to give a glycated hemoglobin value (HbA1c value (%)). Measurement was performed for systems using elimination reagents 1, 2, and 3 separately. As a comparative example, similar measurement was performed with a system that involves using no elimination reagent of B and not performing an elimination step. Table 2 shows the above results.

TABLE 2

Comparison of HbA1c values measured in cases in which no or various contaminants were added

| | HbA1c value (%) | | | |
|---|---|---|---|---|
| Substance added | Comparative example (without elimination) | Present invention (Elimination 1) | Present invention (Elimination 2) | Present invention (Elimination 3) |
| None | 5.8 | 5.8 | 5.8 | 5.8 |
| Fru-Val | 29.0 | 5.8 | 5.8 | 5.8 |
| Fru-Gly | 13.8 | 5.8 | 5.8 | 11.6 |
| ε-Fru-Lys | 11.6 | 5.8 | 12.2 | 5.8 |
| Fru-Val-Leu | 5.8 | 5.8 | 5.8 | 5.8 |
| All substances were added | 43.7 | 5.8 | 12.2 | 11.6 |

Hemoglobin concentration (Hb): 130 g/L

Numerical values included in "Elimination 1," "Elimination 2," and "Elimination 3" are the results of separately using elimination reagents 1, 2, and 3 as elimination reagents.

As shown in Table 1, in the glycated hemoglobin assay system in which no elimination had been performed, the thus measured HbA1c values were significantly higher than the measured value obtained when no substance had been added, directly reflecting the addition of the contaminants. Hence, no precise values were obtained. In particular, measurement errors were significant when an α-amino acid, Fru-Val or Fru-Gly, had been added. The measured value obtained with the use of the system to which all the contaminants had been caused to coexist was 43.7%, whereas the measured value obtained with the use of the system to which no substance had been added was 5.8%. In the presence of the contaminants, measured values that were significantly different from the actual values were obtained. In contrast, in the case of determination comprising an elimination step using elimination reagent 1 of the present invention, no measurement errors took place as a result of all types of contaminant being added, and the obtained values were all consistent with the HbA1c value obtained with the use of the system to which no substance had been added. It could be confirmed that the contaminants can be efficiently eliminated and precise measurement can be performed with the use of the system containing an elimination step using elimination reagent 1 of the present invention.

Elimination reagent 1 of the present invention contains two types of ketoamine oxidase, a type having high specificity to an α-glycated amino acid and a type having high specificity to an ε-glycated amino acid and an ε-glycated peptide. Complete elimination of various contaminants was achieved by the use of elimination reagent 1. Elimination 2 and Elimination 3 are examples in which elimination reagents with compositions differing from that of Elimination 1 were used. Significant improvement in accuracy of measured values can be confirmed with Elimination 2 and Elimination 3, compared with the comparative example. With Elimination 2 and Elimination 3, contaminants remained uneliminated in small amounts because of the substrate specificity of the enzymes for elimination. As is clear from the result of Elimination 1, these contaminants can be completely eliminated by incorporation of known ketoamine oxidase having high specificity to the uneliminated substances into an elimination reagent. In addition to such a method, for example, when ε-Fru-Lys remains uneliminated, the use of FPOX (FPOX-EE, produced by KIKKOMAN CORPORATION (Japan)), which hardly acts on ε-Fru-Lys as an enzyme for determination makes it possible to reduce inclusion of the amount of ε-Fru-Lys in the measured value of a target substance and to reduce measurement errors.

In addition, regardless of presence or the absence or the type of elimination system, the measured values in Examples were never affected by the addition of Fru-Val-Leu. These results reflect the substrate specificity of FPOX used herein. Based on these results, it was thus demonstrated that according to the present invention, various glycated amino acids and/or glycated peptides other than α-glycated peptides can be efficiently eliminated. Furthermore, it was demonstrated that, among α-glycated peptides, Fru-Val-His derived from the "β chain" of glycated hemoglobin and Fru-Val-Leu derived from the "α chain" of glycated hemoglobin are distinguished. It was also demonstrated that Fru-Val-His derived from the "β chain" alone; that is, HbA1c, can be quantitatively determined with accuracy. Hence, according to the present invention, precise quantitative determination of HbA1c is realized through elimination of various contaminants that cause measurement errors.

Example 2

<Confirmation of Effect of Eliminating Contaminant on Human Blood Sample>

Hemoglobin A1c (HbA1c) in human blood samples was used as a glycated protein to be determined herein. The effect of eliminating contaminants generated by liberation and protease treatment was verified using systems for determination of an α-glycated peptide generated by protease treatment using FPOX. Furthermore, it was confirmed in a manner similar to that in Example 1 whether an elimination effect could be confirmed when a contaminant was added after protease treatment. The same experiment was conducted using the method as described in Example 1, except for using human blood samples as HbA1c to be determined. Table 3 shows values obtained by measuring absorbance at 750 nm and then subtracting a change in absorbance of a blank sample from a change in absorbance of a specimen.

TABLE 3

| | Comparative example Without elimination | Present invention Elimination 1 | Present invention Elimination 2 | Present invention Elimination 3 |
|---|---|---|---|---|
| 5.8% HbA1c (control) | 0.024 | 0.014 | 0.024 | 0.016 |
| Human blood cell | 0.028 | 0.021 | 0.028 | 0.022 |
| Human blood cell + Fru-Val | 0.052 | 0.021 | 0.029 | 0.022 |
| Human blood cell + εFru-Lys | 0.039 | 0.021 | 0.039 | 0.022 |

First, in a control experiment, an elimination effect was confirmed when an HbA1c standard substance was used in a manner similar to that in Example 1. For example, an elimination effect was also confirmed in the case of Elimination 3, but the highest elimination effect was confirmed in the case of Elimination 1 (a combination of Elimination 2 and Elimination 3). Almost the same result was obtained when a human blood sample had been used. It was considered that the contaminants contained in the systems had been eliminated successfully in the case of Elimination 1, so that precise HbA1c quantitative determination had become possible.

Furthermore, elimination effects exerted by addition of contaminants to human blood samples were also confirmed. When Fru-Val α-glycated amino acid generated by an infusion solution or the like) having a glycated α-amino group and ε-Fru-Lys (ε-glycated amino acid generated by blood proteins that contaminated the system or protease's own cleavage) having a glycated α-amino group were added as contaminants and then determination was performed without performing elimination according to the present invention, a very high value was obtained. However, when elimination was performed according to the present invention, the effects of the contaminants could be successfully removed. The highest elimination effect was confirmed in the case of Elimination 1, as in the case of a control experiment. It was shown that such value of 0.021 in the case of Elimination 1, "Human blood cell+Fru-Val" and "Human blood cell+ε-Fru-Lys" in Table 3, was equivalent to that obtained when Elimination 1 had been performed without adding any contaminant to human blood cells. This means, for example, that substances that cause measurement errors can be successfully eliminated by the elimination method of the present invention even when a glycated amino acid concentration in human blood is increased due to sugar and amino acid contained in an infusion solution or when an ε-glycated amino acid generated by cleavage of proteins and the like contaminating the system is present.

The above results suggest the usefulness of the method for eliminating contaminants of the present invention.

All publications, patents, and patent applications cited herein are incorporated herein by reference in their entirety.

The invention claimed is:

1. A method for quantitative determination of a glycated protein, comprising (1) allowing a protease to act on a whole blood and/or blood cell sample to provide a mixture of proteolytic products of said sample, (2) allowing an elimination reagent containing at least two types of ketoamine oxidases to act on the mixture, eliminating therefrom an α-glycated amino acid, an ε-glycated amino acid, and an ε-glycated peptide, and then (3) determining an α-glycated peptide in the sample using oxidase that acts on the α-glycated peptide, wherein said types of ketoamine oxidases are selected from the group consisting of (i) an enzyme that acts on the α-glycated amino acid but does not act on the α-glycated peptide, (ii) an enzyme that acts on the ε-glycated amino acid and/or the ε-glycated peptide but does not act on the α-glycated peptide, and (iii) an enzyme that acts on the ε-glycated amino acid and/or the ε-glycated peptide and the α-glycated amino acid but does not act on the α-glycated peptide.

2. The method according to claim 1, wherein the enzyme that acts on the α-glycated amino acid but does not act on the α-glycated peptide is fructosyl amino acid oxidase derived from the genus *Corynebacterium, Arthrobacter,* or *Agrobacterium*.

3. The method according to claim 1, wherein the enzyme that acts on the ε-glycated amino acid and/or the c-glycated peptide but does not act on the α-glycated peptide is fructosyl amino acid oxidase derived from the genus *Fusarium* or *Gibberella*.

4. The method according to claim 1, wherein the enzyme that acts on the ε-glycated amino acid and/or the ε-glycated peptide, and the α-glycated amino acid, but does not act on the α-glycated peptide is ketoamine oxidase derived from the genus *Gibberella, Fusarium, Penicillium, Aspergillus, Candida, Acremonium, Debaryomyces, Pichia, Trichosporon,* or *Bacillus*.

5. The method according to claim 1, wherein the oxidase that acts on the α-glycated peptide is fructosyl peptide oxidase.

6. The method according to claim 1, wherein the glycated protein is glycated hemoglobin.

* * * * *